US008954151B2

(12) United States Patent
Lopez et al.

(10) Patent No.: US 8,954,151 B2
(45) Date of Patent: Feb. 10, 2015

(54) RF RESISTANT FEEDTHROUGH ASSEMBLY AND ELECTRICAL STIMULATION SYSTEMS CONTAINING THE ASSEMBLY

(71) Applicant: Boston Scientific Neuromodulation Corporation, Valencia, CA (US)

(72) Inventors: Thomas Lopez, Sunland, CA (US); Matthew Lee McDonald, Pasadena, CA (US); Gaurav Gupta, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/166,672

(22) Filed: Jan. 28, 2014

(65) Prior Publication Data

US 2014/0214130 A1    Jul. 31, 2014

Related U.S. Application Data

(60) Provisional application No. 61/758,104, filed on Jan. 29, 2013.

(51) Int. Cl.
*A61N 1/375* (2006.01)
(52) U.S. Cl.
CPC .................................... *A61N 1/3754* (2013.01)
USPC .......................................................... 607/37
(58) Field of Classification Search
None
See application file for complete search history.

(56) References Cited

U.S. PATENT DOCUMENTS

| | | | |
|---|---|---|---|
| 5,336,246 A * | 8/1994 | Dantanarayana | 607/37 |
| 5,825,608 A * | 10/1998 | Duva et al. | 361/302 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2007/0150036 A1 | 6/2007 | Anderson | |

* cited by examiner

*Primary Examiner* — Brian T Gedeon
(74) *Attorney, Agent, or Firm* — Lowe Graham Jones PLLC; Bruce E. Black (57) ABSTRACT

A control module for an electrical stimulation system includes a casing having an electrically-conductive portion; an electronic subassembly disposed in the casing; and a header portion coupled to the casing and including a connector for a lead or lead extension. The control module also includes a feedthrough assembly coupling the casing to the header portion. The feedthrough assembly includes a non-conductive ceramic block; conductive feedthrough pins passing through the ceramic block and electrically coupling the connector to the electronic subassembly disposed in the casing; a metal flange disposed around, and attached to, the ceramic block, and a non-conductive spacer attached to the metal flange and to the casing to raise the ceramic block above, and away from, the casing. Other control modules include a ceramic block that has a rim portion that raises the plate portion, through which the feedthrough pins pass, of the block away from the casing.

8 Claims, 7 Drawing Sheets

RF RESISTANT FEEDTHROUGH ASSEMBLY AND ELECTRICAL STIMULATION SYSTEMS CONTAINING THE ASSEMBLY

CROSS-REFERENCE TO RELATED APPLICATIONS

This application claims the benefit under 35 U.S.C. §119 (e) of U.S. Provisional Patent Application Ser. No. 61/758,104 filed Jan. 29, 2013, which is incorporated herein by reference.

FIELD

The present invention is directed to the area of implantable electrical stimulation systems and methods of making and using the systems. The present invention is also directed towards feedthrough assemblies that are RF resistant and implantable electrical stimulation systems containing the feedthrough assemblies as well as methods of making and using the feedthrough assembly and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

The pulse generators typically planted within the patient's body have an outer casing and a header made of bio-compatible material. The electronic components such as RF transceivers inside the casing are interfaced with the lead through a hermetically sealed assembly known as a feedthrough assembly. Strong electromagnetic environments, such as MRI (magnetic resonance imaging) scans, can produce induced RF currents that may be detrimental.

BRIEF SUMMARY

One embodiment is a control module for an electrical stimulation system that includes a casing defining an inner space and having at least one electrically-conductive portion; an electronic subassembly disposed in the inner space of the casing and having a pulse generator; and a header portion coupled to the casing and including a connector for receiving a proximal end of at least one lead or lead extension. The connector includes conductive contacts for electrically coupling to terminal contacts on the at least one lead or lead extension. The control module also includes a feedthrough assembly coupling the casing to the header portion and, in combination with the casing, sealing the inner space of the casing. The feedthrough assembly includes a non-conductive ceramic block having a first surface facing the inner space of the casing, a second surface, opposite the first surface, facing the header portion, and a side surface disposed between, and connecting, the first and second surfaces; conductive feedthrough pins passing through the ceramic block from the first surface to the second surface and electrically coupling the conductive contacts of the connector to the electronic subassembly disposed in the inner space of the casing; a metal flange disposed around, and attached to, the side surface of the ceramic block; and a non-conductive spacer attached to the metal flange and to the casing to raise the ceramic block above, and away from, the casing.

Another embodiment is a control module for an electrical stimulation system that includes a casing defining an inner space and having at least one electrically-conductive portion; an electronic subassembly disposed in the inner space of the casing and having a pulse generator; and a header portion coupled to the casing and including a connector for receiving a proximal end of at least one lead or lead extension. The connector includes conductive contacts for electrically coupling to terminal contacts on the at least one lead or lead extension. The control module also includes a feedthrough assembly coupling the casing to the header portion and, in combination with the casing, sealing the inner space of the casing. The feedthrough assembly includes a non-conductive ceramic block having a plate portion and a rim portion; conductive feedthrough pins passing through the plate portion of the ceramic block and electrically coupling the conductive contacts of the connector to the electronic subassembly disposed in the inner space of the casing; and a metal ring attached to the casing and disposed around, and attached to, part of the rim portion of the ceramic block to couple the ceramic block to the casing. The plate portion of the ceramic block has a circumference, a first surface, and a second surface opposite the first surface. The rim portion is disposed around the circumference of the plate portion and extends away from the second surface of the plate portion. The rim portion and the second surface of the plate portion define an interior space.

Yet another embodiment is a control module for an electrical stimulation system that includes a casing defining an inner space and having at least one electrically-conductive portion; an electronic subassembly disposed in the inner space of the casing and having a pulse generator; and a header portion coupled to the casing and including a connector for receiving a proximal end of at least one lead or lead extension. The connector includes conductive contacts for electrically coupling to terminal contacts on the at least one lead or lead extension. The control module further includes a feedthrough assembly coupling the casing to the header portion and, in combination with the casing, sealing the inner space of the casing. The feedthrough assembly includes a non-conductive ceramic block having a circumference, a first surface, and a second surface opposite the first surface; a metal flange attached to the casing or forming a portion of the casing and disposed around the circumference of the ceramic block; and conductive feedthrough pins passing through the ceramic block from the first surface and electrically coupling the conductive contacts of the connector to the electronic subassembly disposed in the inner space of the casing. The feedthrough pins are disposed in a staggered arrangement with each of the feedthrough pins separated from a nearest adjacent one of the feedthrough pins by a distance that is at least 10% less than a distance from the feedthrough pin to a nearest portion of the metal flange.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed towards feedthrough assemblies that are RF resistant and implantable electrical stimulation systems containing the feedthrough assemblies as well as methods of making and using the feedthrough assembly and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
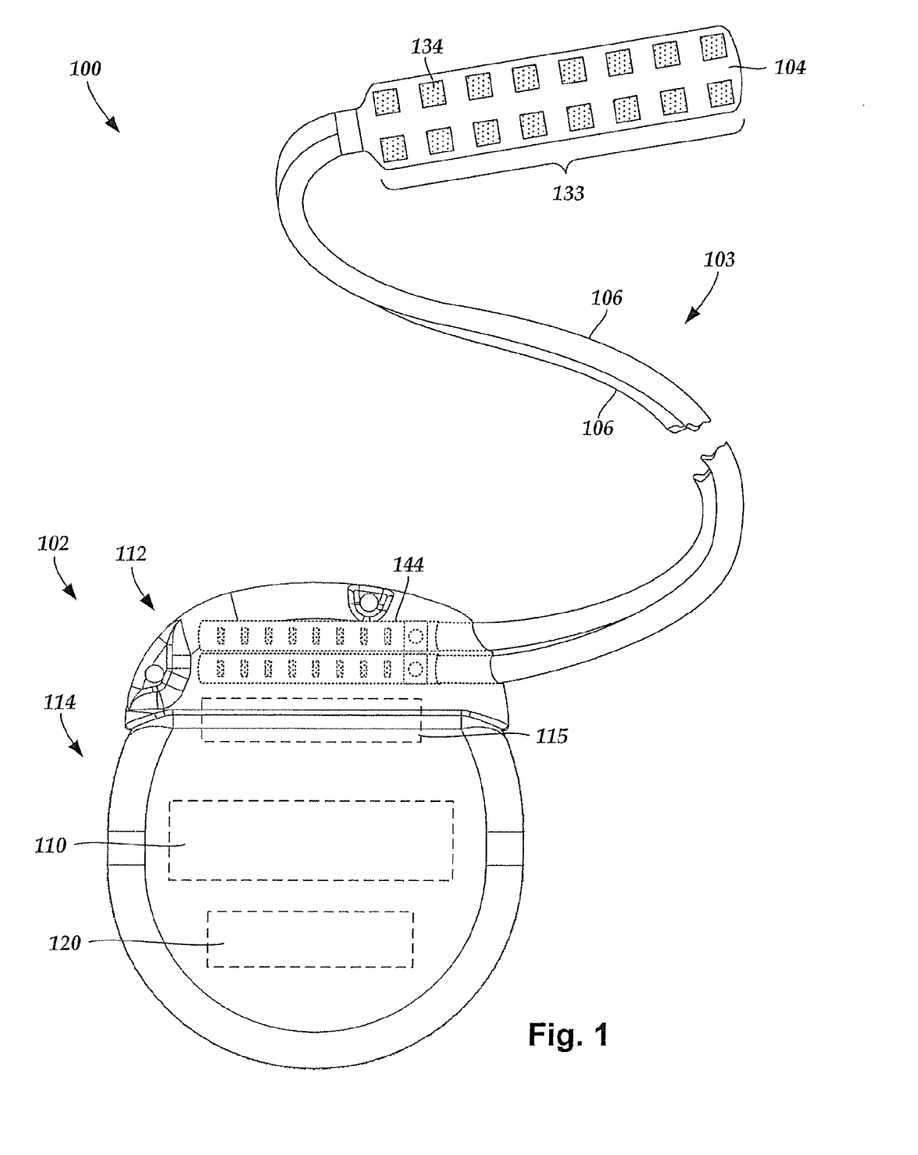
FIG. 1 is a schematic side view of an embodiment of an electrical stimulation system that includes a paddle lead electrically coupled to a control module, according to the invention.

FIG. 1 illustrates schematically an embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIG. 3) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
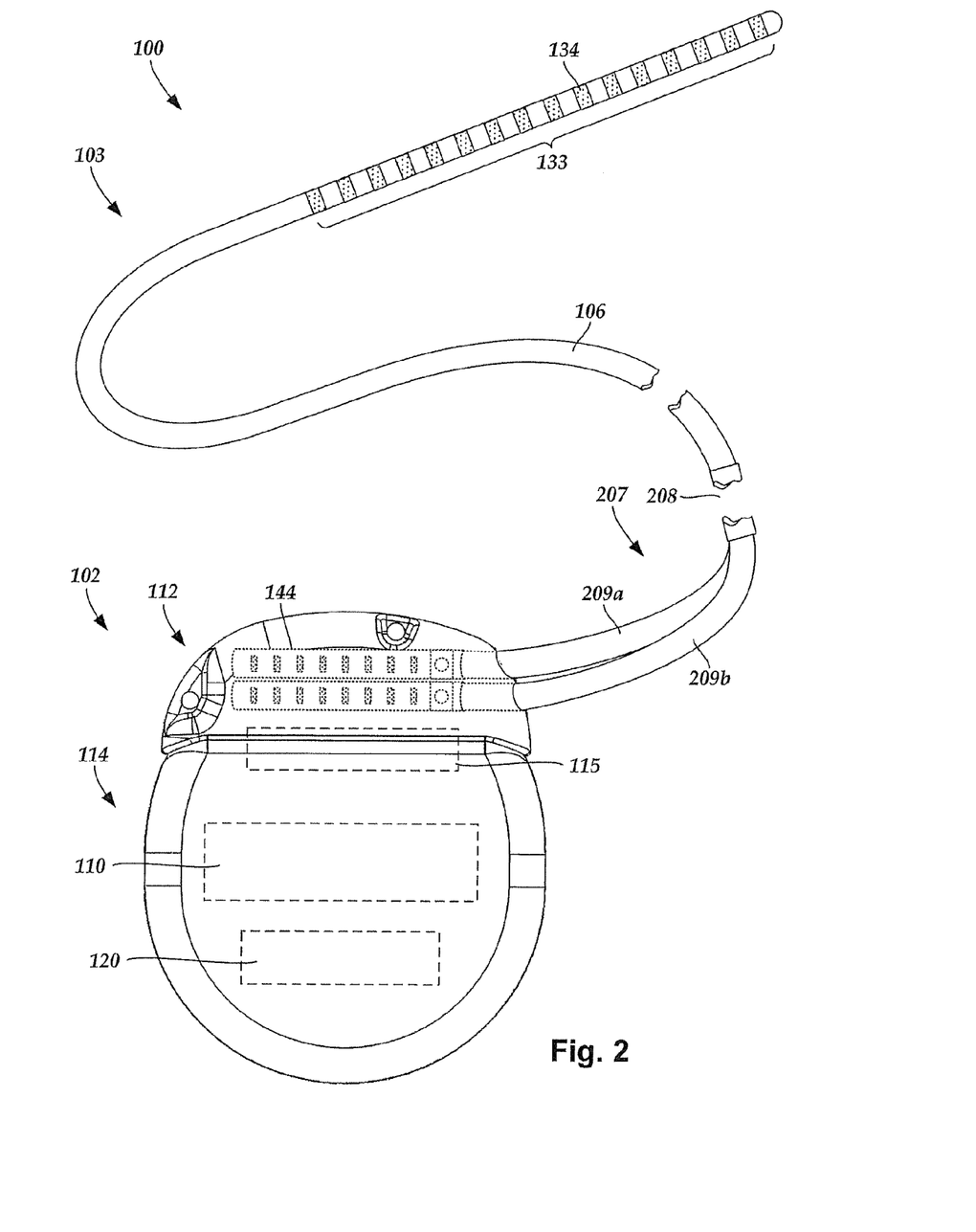
FIG. 2 is a schematic side view of an embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a header portion 112 and a sealed casing 114. The casing 114 may be formed, at least in part, of metal or have a metal coating disposed on at least a portion of the casing. An electronic subassembly 110 and an optional power source 120 are disposed in the casing 114. A control module connector 144 is disposed in the header portion 112. The control module connector 144 is configured and arranged to make an electrical connection between the lead 103 and the electronic subassembly 110 of the control module 102. The control module also includes a feedthrough assembly 115 for electrically coupling the connector 144 of the header portion 112 to the internal electronic subassembly 110 in the casing 114

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 and may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
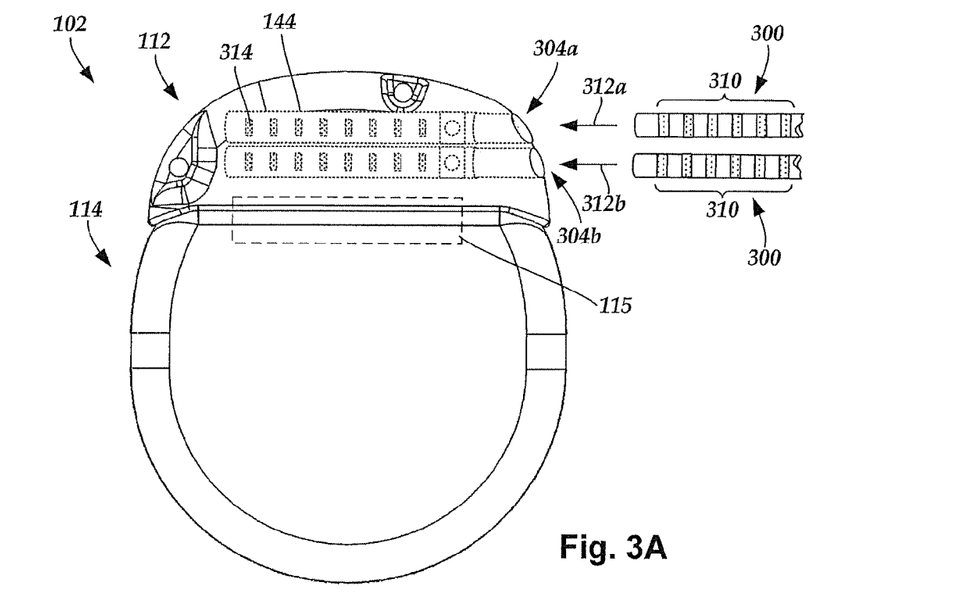
FIG. 3A is a schematic side view of an embodiment of the control module of FIG. 1 configured and arranged to electrically couple to an elongated device, according to the invention.
Figure 3B:
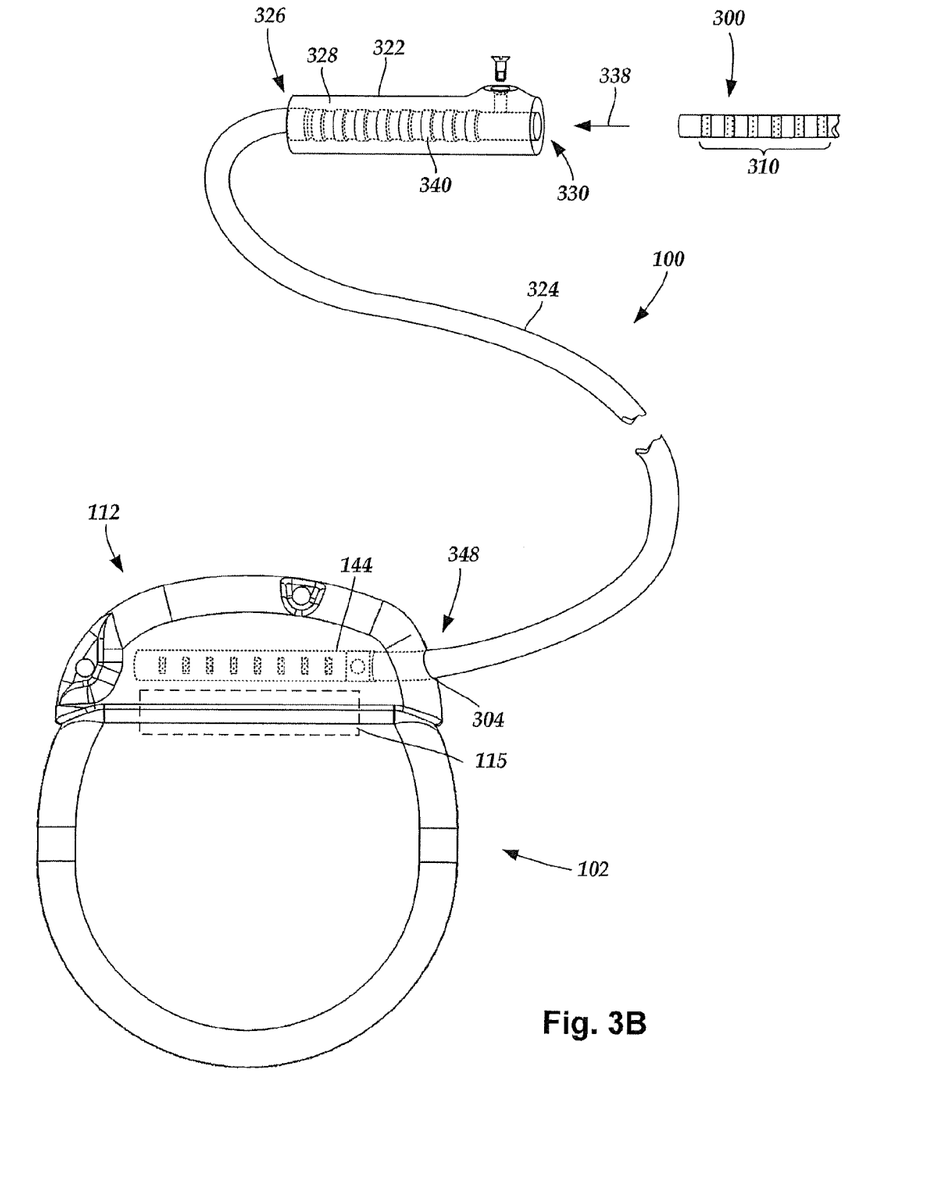
FIG. 3B is a schematic side view of an embodiment of a lead extension configured and arranged to electrically couple the elongated device of FIG. 2A to the control module of FIG. 1.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the header portion 112 is shown having two ports 304a and 304b. The header portion 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 200, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144. The header portion 112 housing the control module connector 144 may not be hermetically sealed as the lead(s) 106 are inserted into the port(s) 304 of the header portion 112.

A feedthrough assembly 115 is structured and arranged as an interface between the control module connector 144 and the electronic sub-assembly 110 enclosed by the casing 114. The feedthrough assembly 115 along with the casing 114 hermetically seals the electronic sub-assembly 110 and also electrically couples the electronic sub-assembly 110 with the connector contacts 314 of the control module connector 144.

The feedthrough assembly 115 includes conductive pins that provide electrically connectivity between the connector contacts 314 in the control module connector 144 and the electronic subassembly 110. In at least some conventional control modules, the feedthrough assembly includes conductive pins electrically isolated by a ceramic block or bushings and supported by a metallic flange wrapped around the periphery of the ceramic block. The metal flange enables the feedthrough assembly to be connected to the outer casing of the control module. Strong electromagnetic environments, such as MRI scans, may produce induced RF current within the lead or control module. Stray capacitance, with relatively low impedance, between the conductive pins inserted in the ceramic block and the outer casing of these conventional control modules can provide a discharge path for the induced RF currents. Discharge of the induced RF currents through the outer casing of the control module may result in undesirable effects such as heating of the tissue around the control module.

The impedance of this discharge path can be increased (and the corresponding stray capacitance decreased) by increasing the effective distance between the conductive pins of the feedthrough assembly 115 and the outer casing 114 of the control module 102. In some embodiments, the distance between the conductive pins and the casing 114 is increased by elevating the feedthrough assembly 115 away from the casing 114. This can be accomplished, for example, by incorporation of a non-conductive spacer.

Figure 4:
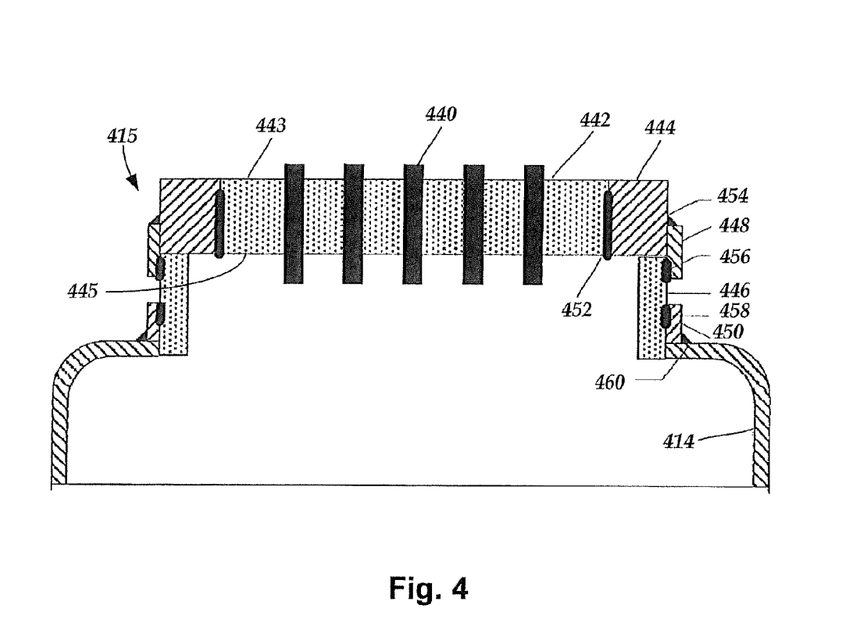
FIG. 4 is a schematic cross-sectional view of a first embodiment of a feedthrough assembly and a portion of a casing of a control module, according to the invention.

FIG. 4 illustrates one embodiment of a feedthrough assembly 415 raised above an opening in the control module (102 as shown in FIG. 3B) designed to seat the feedthrough assembly 415. The feedthrough assembly 415 is raised toward the header portion (112 as shown in FIG. 3B) and away from the casing 414.

The feedthrough assembly 415 includes a ceramic block 442 that cooperates with the casing 414 to seal the electronic subassembly inside the casing 414. In the illustrated embodiment, the ceramic block 442 has a horizontal alignment relative to the control module (102 as shown in FIG. 3B), but other alignments such as, but not limited to, a vertical or angular orientation can be used depending upon the structure and shape of the control module (102 as shown in FIG. 3B) and associated casing 414.

The ceramic block 442 is formed from a non-conductive material to provide electric isolation among the conductive pins 440. The ceramic block 442 may define a substantially rectangular cross-section. In at least some embodiments, one side of the ceramic block 442 defines a relatively horizontal surface facing an inner space of the casing 414, while another horizontal surface, lying opposite to the first horizontal surface, faces the header portion. It will be understood that the ceramic block 442 may have other shapes.

Conductive feedthrough pins 440 are inserted through the ceramic block 442. Any suitable placement and alignment of the feedthrough pins 440 with respect to the horizontal surfaces can be used. The dimensions of feedthrough pins 440 may be selected based on, but not limited to, the thickness of the ceramic block 442 through which they pass. The feedthrough pins 440 are made of an electrically conductive material that preferably provides a suitable impedance match between the connector contacts (314 as shown in FIG. 3A) of the connector (144 as shown in FIG. 3A) and the electronic subassembly (110 as shown in FIG. 2) enclosed in the casing 414.

The ceramic block 442 is coupled to a metal flange 444 to hold and support the ceramic block. Adhesion between ceramic block 442 and metal flange 444 may be achieved through a braze joint 452 of the side surfaces of the ceramic block 442 with the metal flange 444.

A non-conductive spacer 446 is placed between the metal flange 444 and the casing 414 to increase the distance between the casing and the pins 440 in the feedthrough assembly 415. In at least some embodiments, the non-conductive spacer 446 has a height of at least 1 mm, 2 mm, 2.5 mm, 3 mm, 4 mm, or at least 5 mm or more.

The non-conductive spacer 446 may be perpendicularly aligned to the metal flange 444 in such a manner that a portion of the metal flange 444 rests on one end of the non-conductive spacer 446. Alternatively or additionally, a portion of the ceramic block 442 may rest on the non-conductive spacer 446. The non-conductive spacer 446 can be made of a ceramic composition or any other suitable material that provides electric isolation between the metal flange 444 and the casing 414. The non-conductive spacer 446 raises the ceramic block 442 and feedthrough pins 440 away from the casing 414 towards the header portion (112 as shown in FIG. 3A).

In some embodiments, the non-conductive spacer 446 can be joined to the metal flange 444 by a braze joint. In the illustrated embodiment, however a first metal ring 448 is placed around adjoining portions of the metal flange 444 and the non-conductive spacer 446 to couple these two components together. In the illustrated embodiment, a weld joint 454 is used to join the first metal ring 448 to the metal flange 444. Any suitable weld joint can be used including, but not limited to, a tee joint, a corner joint, a butt joint, or a lap joint. It will also be recognized that any other suitable method for joining the first metal ring 448 to the metal flange 444 can be used.

In the illustrated embodiment, the first metal ring 448 is joined to the non-conductive spacer 446 through a braze 456. It will also be recognized that any other suitable method for joining the first metal ring 448 to the non-conductive spacer 446 can be used.

In the illustrated embodiment, a second metal ring 450 is similarly use to attach the non-conductive spacer 446 to the casing 414. A weld joint 460, or any other suitable arrangement, can be used to join the second metal ring 450 to the casing and a braze joint 458, or any other suitable arrangement, can be used to join the second metal ring 450 to the non-conductive spacer 446.

Figure 5:
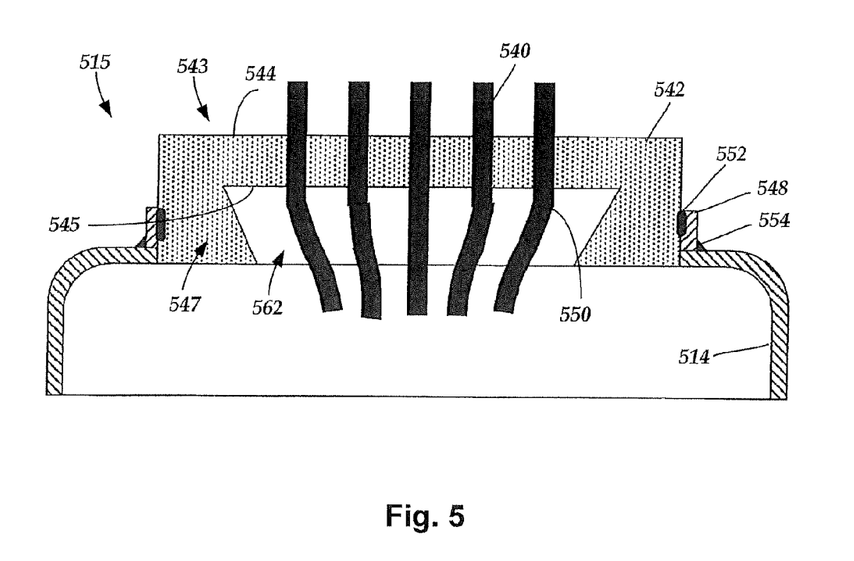
FIG. 5 is a schematic cross-sectional view of a second embodiment of a feedthrough assembly and a portion of a casing of a control module, according to the invention.

FIG. 5 illustrates a second embodiment of a feedthrough assembly 515 mounted on a casing 514. A relatively large dimensional ceramic block 542, compared to conventional feedthrough assemblies, is used to increase the distance between feedthrough pins 540 and the casing 514. Structurally, the ceramic block 542 can be divided into two portions, a plate portion 543 and a rim portion 547. The plate portion 543 is characterized by a first horizontal surface 544, facing the header portion (112 as shown in FIG. 3A) and a second horizontal surface 545 opposite the first horizontal surface 544. A number of conductive feedthrough pins 540 pass through the plate portion 543.

The rim portion 547 is disposed around the circumference of the plate portion 543 and extends away from the second horizontal surface 545 of the plate portion. The rim portion 547 effectively separates the plate portion 543 and the feedthrough pins 540 from the casing 514. In at least some embodiments, the height of the plate portion (measured from the bottom of the plate portion to the second horizontal surface 545) is at least 1 mm, 2 mm, 2.5 mm, 3 mm, 4 mm, or at least 5 mm or more.

The rim portion 547 and the second horizontal surface 545 of the plate portion 543 define an interior space 562, as shown in FIG. 5. In at least some embodiments, an inner wall of the rim portion 547 has an angular slope such that the second horizontal surface 545 and the inner wall of the rim portion 547 define an acute angle with respect to each other. This angle may be, for example, in the range of 60 to 85 degrees. In at least some embodiments, the inner wall of the rim portion 547 has a converging profile when extending towards the electronic sub-assembly (110 as shown in FIG. 2).

The feedthrough pins 540 emerging through the second horizontal surface 545 of the ceramic block 542 and into the interior space 562 can be connected to conductive wires 550 or one or more flexible circuit boards that extend to the electronic sub-assembly (110 as shown in FIG. 2). In at least some embodiments, the conductive wires 550, or the feedthrough pins 540 or the flexible circuit board(s), are pulled towards the centre of the interior space 562, closer to each other and away from the casing 514.

Although the ceramic block could be coupled to the casing using a braze joint, in the illustrated embodiment a metal ring 548 is used to connect the ceramic block 542 with the casing 514. The metal ring 548 is disposed around the periphery of the ceramic block 542 and attaches to the rim portion 547 of the ceramic block through a braze joint 552. Any other suitable arrangement for coupling the ceramic block 542 to the metal ring 548 can be used instead of the braze joint 552. The metal ring 548 is connected to the casing 514 through a weld joint 554. Any other suitable arrangement for coupling the casing 514 to the metal ring 548 can be used instead of the weld joint 554.

Figure 6:
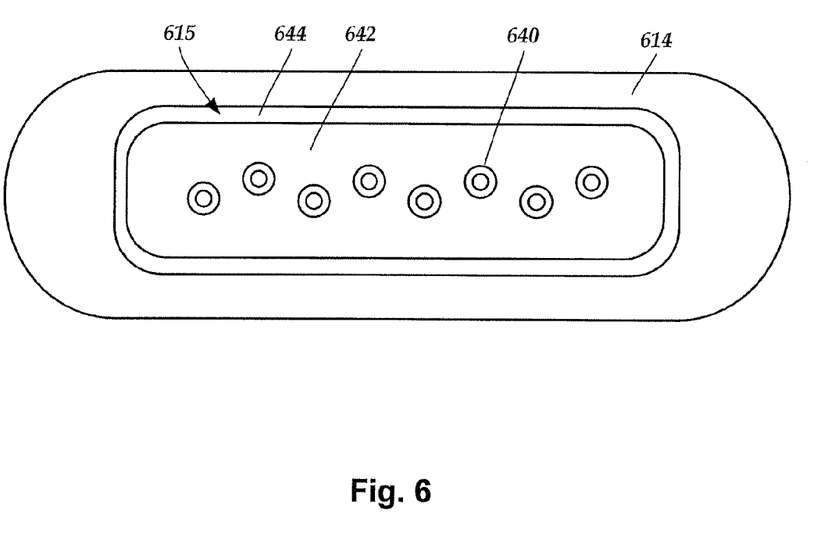
FIG. 6 is a schematic top view of a third embodiment of a feedthrough assembly and a portion of a casing of a control module, according to the invention.

FIG. 6 illustrates a third embodiment of a feedthrough assembly 615 and a portion of a casing of 614 of a control module (102 as shown in FIG. 3B). The feedthrough assembly 615 includes a ceramic block 642 with a number of feedthrough pins 640 passing through the ceramic block 642 to electrically couple to the electronic subassembly (110 as shown in FIG. 2) encased within the casing 614. A metal flange 644 is disposed around the periphery of the ceramic block 642. The metal flange 644 is connected to the ceramic block 642 and also to the casing 614 using a braze joint or any other suitable arrangement.

The feedthrough pins 640 are positioned on the ceramic block 642 such that adjacent feedthrough pins 640 are diagonally disposed to each other, relative to a horizontal axis of the feedthrough assembly 615, thus resulting in a symmetrical staggered arrangement. In at least some embodiments, the angle between the diagonally arranged feedthrough pins 640 is kept substantially small to ensure that the distance between adjacent feedthrough pins 640 is at least 10%, 15%, 25%, 30%, 40%, or 50% less than the distance between the feedthrough pin 640 and the nearest portion of the metal flange 644. The staggered arrangement of the feedthrough pins 640, as opposed to a linear arrangement of pins, can result in a feedthrough assembly 615 with smaller lateral length. The restricted angular disposition of the feedthrough pins 640, on the other hand, maintains a relatively large distance, compared to conventional staggered pin arrangements, between the pins and the surrounding metal flange 644 and casing 614, thereby reducing the stray capacitance between the pins and the casing.

Figure 7:
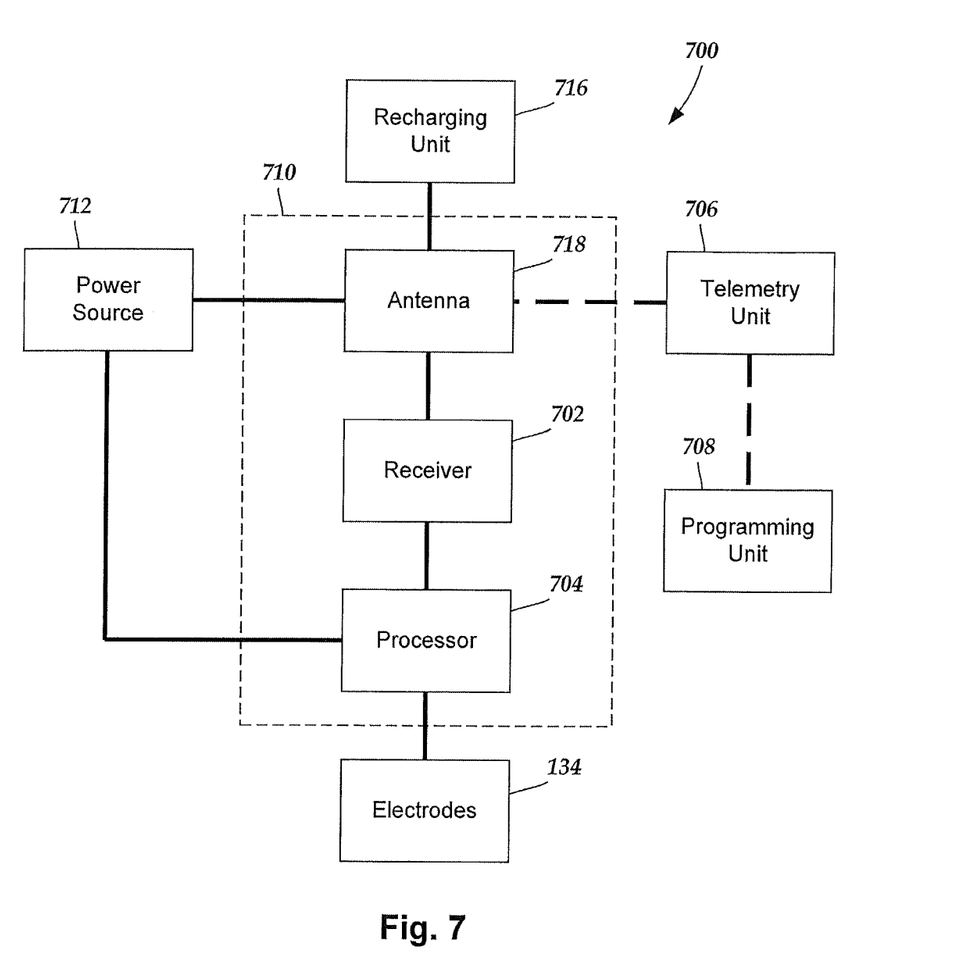
FIG. 7 is a schematic overview of an embodiment of components of a stimulation system, including an electronic subassembly disposed within a control module, according to the invention.

FIG. 7 is a functional block overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A control module for an electrical stimulation system, comprising:
    a casing defining an inner space, the casing comprising at least one electrically-conductive portion;
    an electronic subassembly disposed in the inner space of the casing, the electronic subassembly comprising a pulse generator;
    a header portion coupled to the casing and comprising a connector configured and arranged to receive a proximal end of at least one lead or lead extension, the connector comprising a plurality of conductive contacts configured and arranged to electrically couple to terminal contacts on the at least one lead or lead extension;
    a feedthrough assembly coupling the casing to the header portion and, in combination with the casing, sealing the inner space of the casing, the feedthrough assembly comprising
        a non-conductive ceramic block having a first surface facing the inner space of the casing, a second surface, opposite the first surface, facing the header portion, and a side surface disposed between, and connecting, the first and second surfaces,
        a plurality of conductive feedthrough pins passing through the ceramic block from the first surface to the second surface, the feedthrough pins electrically coupling the conductive contacts of the connector to the electronic subassembly disposed in the inner space of the casing,
        a metal flange disposed around, and attached to, the side surface of the ceramic block, and
        a non-conductive spacer attached to the metal flange and to the casing to raise the ceramic block above, and away from, the casing.

2. The control module of claim 1, wherein the metal flange is brazed to the ceramic block.

3. The control module of claim 1, wherein the feedthrough assembly further comprises a first metal ring that attaches the metal flange to the non-conductive spacer.

4. The control module of claim 3, wherein the feedthrough assembly further comprises a second metal ring that attaches the non-conductive spacer to the casing.

5. The control module of claim 1, wherein the non-conductive spacer is a ceramic spacer.

6. The control module of claim 1, wherein the metal flange is seated on top of the non-conductive spacer.

7. The control module of claim 1, wherein the feedthrough assembly and the casing hermetically seal the inner space of the casing.

8. An electrical stimulation system, comprising
    the control module of claim 1; and
    a lead having a proximal end configured and arranged to be received in the connector of the control module.

* * * * *